(12) United States Patent
Guthrie et al.

(10) Patent No.: US 9,109,253 B2
(45) Date of Patent: Aug. 18, 2015

(54) OLIGONUCLEOTIDES AND METHODS FOR DETECTING LAVENDER FOAL SYNDROME

(75) Inventors: Alan John Guthrie, Swavelport (ZA); Cindy Kim Harper, Swavelport (ZA); Anandi Bierman, Faerie Glen (ZA)

(73) Assignee: University of Pretoria, Pretoria (SA)

( * ) Notice: Subject to any disclaimer, the term of this patent is extended or adjusted under 35 U.S.C. 154(b) by 0 days.

(21) Appl. No.: 13/512,536

(22) PCT Filed: Dec. 1, 2010

(86) PCT No.: PCT/IB2010/055529
§ 371 (c)(1),
(2), (4) Date: Oct. 2, 2012

(87) PCT Pub. No.: WO2011/067725
PCT Pub. Date: Jun. 9, 2011

(65) Prior Publication Data
US 2013/0022972 A1   Jan. 24, 2013

(30) Foreign Application Priority Data
Dec. 2, 2009 (ZA) .................................. 2009/08541

(51) Int. Cl.
*C07H 21/04* (2006.01)
*C12Q 1/68* (2006.01)
(52) U.S. Cl.
CPC ........ *C12Q 1/6883* (2013.01); *C12Q 2600/156* (2013.01)
(58) Field of Classification Search
None
See application file for complete search history.

(56) References Cited

U.S. PATENT DOCUMENTS

2011/0023157 A1* 1/2011 Bedell et al. .................... 800/14
2013/0022972 A1* 1/2013 Guthrie et al. ............... 435/6.11

OTHER PUBLICATIONS http://risingrainbow.blogspot.com/2007/06/breeding-carriers-of-lavender-foal.html, Jun. 17, 2007.*
http://www.laboklin.co.uk/laboklin/showGeneticTest.jsp?testID=8301HGD, copyright date 2007.*
Website VHL, Artnr P854 test for Lavender Foal Syndrome. 2008.*
Gabreski et al. J. of Equine Veterinary Science, vol. 29, Issue 5, pp. 321-322, May 2009.*
Bierman, http://web.up.ac.za/defaultasp?ipkCategoryID=11671&articleID=3268, Posted Nov. 4, 2009.*
Brooks et al. (PLoS Genetics, vol. 6, No. 4, pp. e0000909 Apr. 15, 2010).*
Genbank Accession No. HM063929, Jun. 2, 2010.*
Glaser et al. "Lavender Foal Syndrome Genetic Test" Animal Health Diagnostic Center, Aug. 26, 2010.*
Bierman et al. Animal Genetics, vol. I 41, Supple 2, pp. 199-2001, Nov. 10, 2010, online.*
http://web.archive.org/web/20120829113422/http://www.vgl.ucdavis.edu/services/horse.php, Wayback Machine Date Aug. 29, 2012.*
Anonymous; Artnr. P854—Lavender Foal Syndrome (LFS); Dr. van haeringen laboratorium b.v.; 2008; XP002631759.

(Continued)

*Primary Examiner* — Jeanine A Goldberg
(74) *Attorney, Agent, or Firm* — Barnes & Thornburg LLP; Alice O. Martin

(57) ABSTRACT

A method for detecting a genetic polymorphism associated with Lavender Foal Syndrome or a predisposition thereto in a subject, the method including screening a genomic material sample from the subject for the presence of at least one polymorphism in a MYO5A gene.

6 Claims, 1 Drawing Sheet

(56) References Cited

OTHER PUBLICATIONS

Anonymous; Lavender Foal Syndrome (LFS) / Coat Colour Dilution Lethal (CCDL); Laboklin; 2007; pp. 1-4; XP002631758.

Bierman et al.; Equus caballus nonfunctional myosin 5A, partial sequence; Jun. 2, 2010; XP002631764.

Bierman; Lavender Foal Syndrome—genetic test developed in South Africa; The Onderstepoort Veterinary Genetics Laboratory; Nov. 4, 2009; XP002631760.

Bierman et al.; Lavender foal syndrome in Arabian horses is caused by a single-base deletion in the MYO5A gene; Animal Genetics; Dec. 1, 2010; pp. 199-201; vol. 41, Suppl. 2; XP002631762.

Brooks et al.; Whole-Genome SNP Association in the Horse: Identification of a Deletion in Myosin Va Responsible for Lavender Foal Syndrome; PLOS Genetics; Apr. 2010; pp. 1-7; vol. 6, No. 4; XP002631763.

Loubery et al.; Myosins in the secretory pathway: tethers or transporters?; CMLS Cellular and Molecular Life Sciences; Aug. 26, 2008; pp. 2790-2800; vol. 65, No. 18; Berkhauser-Verlag, BA.

Reck-Peterson et al.; Class V myosins; Biochimica et Biophysica Acta. Molecular Cell Research; Mar. 17, 2000; pp. 36-51; vol. 1496, No. 1.

Schott et al.; Cutaneous Markers of Disorders Affecting Young Horses; Clinical Techniques in Equine Practice; Dec. 1, 2005; pp. 314-323; vol. 4, No. 4.

Takagishi et al.; Myosin Va Mutation in Rats is an Animal Model for the Human Hereditary Neurological Disease, Griscelli Syndrome Type 1; Annals for the New York Academy of Sciences; Nov. 2006; pp. 66-80; vol. 1086; XP-002631761.

Search Report and Written Opinion for International Patent Application No. PCT/IB2010/055529; May 26, 2011.

\* cited by examiner

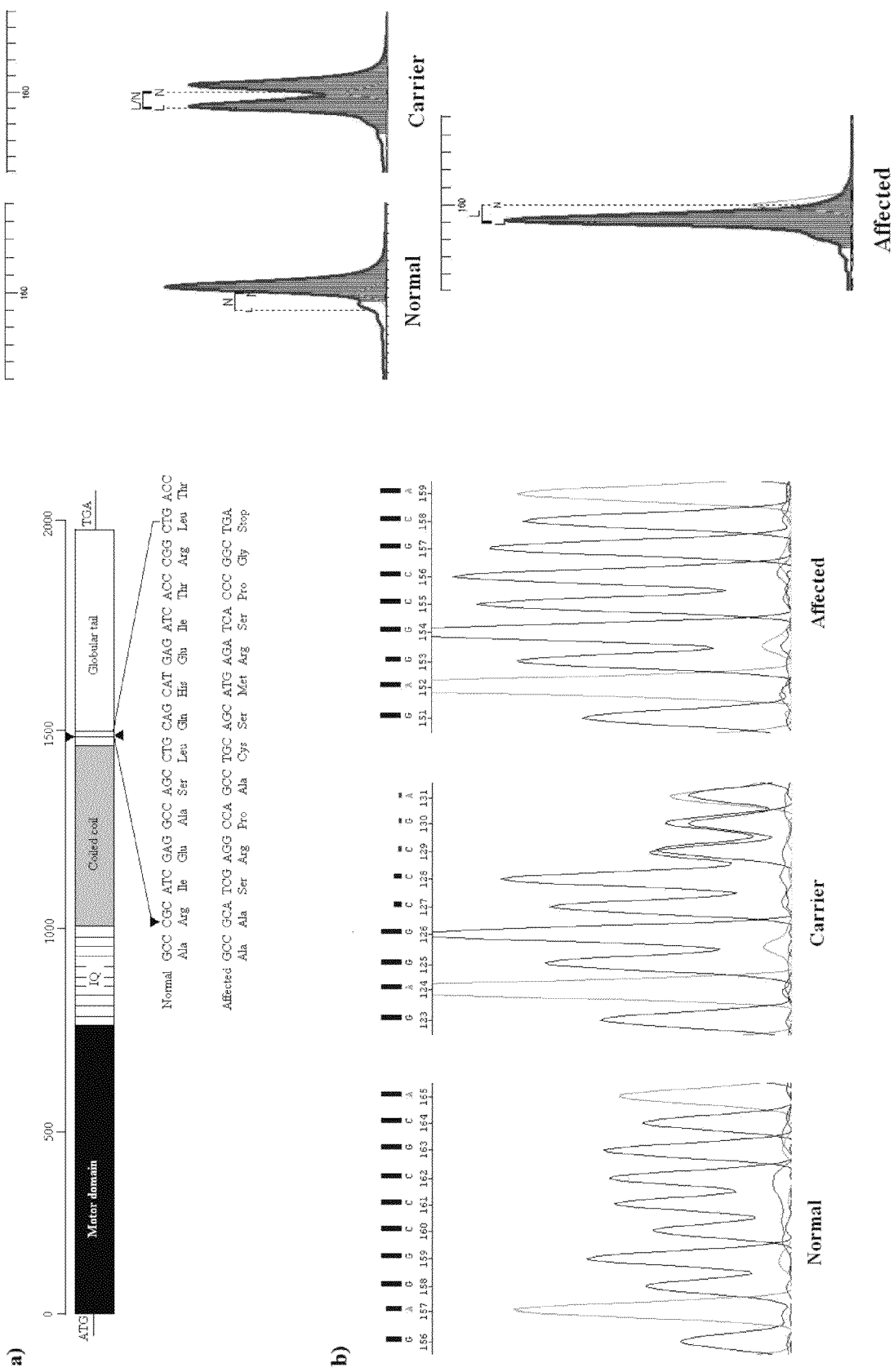

_US 9,109,253 B2_

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
aagacaaagc gcatgccacc                                                   20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
gccgcattct tcagcatcca                                                   20

<210> SEQ ID NO 3
<211> LENGTH: 22
```

```
<212> TYPE: DNA
<213> ORGANISM: Artificial
<220> FEATURE:
<223> OTHER INFORMATION: Primer

<400> SEQUENCE: 3
tccagatgct gtgtcttgtg ca                                              22

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
tcacagtcca ctcagacagc aa                                              22

<210> SEQ ID NO 5
<211> LENGTH: 22
<212> TYPE: DNA
<213> ORGANISM: Artificial
<220> FEATURE:
<223> OTHER INFORMATION: Primer

<400> SEQUENCE: 5
tacagtggtc agaacatggg tg                                              22

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
aaacagagct tccaccaacc                                                 20

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
gctggaatcc ttcacttagg ca                                              22

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
acaggtattg tgcagctgtc                                                 20

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
```
tgactatggg caaagtgcag g    21

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
gtaggaacct ctcccatcag ga    22

<210> SEQ ID NO 11
<211> LENGTH: 22
<212> TYPE: DNA
<213> ORGANISM: Artificial
<220> FEATURE:
<223> OTHER INFORMATION: Primer

<400> SEQUENCE: 11
ccttgcagat actccgtgag ca    22

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
atgctccact tctagggctc    20

<210> SEQ ID NO 13
<211> LENGTH: 22
<212> TYPE: DNA
<213> ORGANISM: Artificial
<220> FEATURE:
<223> OTHER INFORMATION: Primer

<400> SEQUENCE: 13
ctagggtcat ctccgtttcc ta    22

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
ccaagttttc gttggtcagc    20

<210> SEQ ID NO 15
<211> LENGTH: 22
<212> TYPE: DNA
<213> ORGANISM: Artificial
<220> FEATURE:
<223> OTHER INFORMATION: Primer

<400> SEQUENCE: 15
tttagccaga tggtggctcc ac    22

<210> SEQ ID NO 16
<211> LENGTH: 22
<212> TYPE: DNA
<213> ORGANISM: Artificial

<220> FEATURE:
<223> OTHER INFORMATION: Primer

<400> SEQUENCE: 16
tttccactcc acagagacca gg                                          22

<210> SEQ ID NO 17
<211> LENGTH: 22
<212> TYPE: DNA
<213> ORGANISM: Artificial
<220> FEATURE:
<223> OTHER INFORMATION: Primer

<400> SEQUENCE: 17
accaggattc acatgtcccc ac                                          22

<210> SEQ ID NO 18
<211> LENGTH: 22
<212> TYPE: DNA
<213> ORGANISM: Artificial
<220> FEATURE:
<223> OTHER INFORMATION: Primer

<400> SEQUENCE: 18
aaggtgtcgg ttaagactgg ga                                          22

<210> SEQ ID NO 19
<211> LENGTH: 22
<212> TYPE: DNA
<213> ORGANISM: Artificial
<220> FEATURE:
<223> OTHER INFORMATION: Primer

<400> SEQUENCE: 19
gttgcattga cattgctgtt gg                                          22

<210> SEQ ID NO 20
<211> LENGTH: 22
<212> TYPE: DNA
<213> ORGANISM: Artificial
<220> FEATURE:
<223> OTHER INFORMATION: Primer

<400> SEQUENCE: 20
atctactggt gggcacatga gg                                          22

<210> SEQ ID NO 21
<211> LENGTH: 22
<212> TYPE: DNA
<213> ORGANISM: Artificial
<220> FEATURE:
<223> OTHER INFORMATION: Primer

<400> SEQUENCE: 21
agcacacgaa cttaaccact cg                                          22

<210> SEQ ID NO 22
<211> LENGTH: 22
<212> TYPE: DNA
<213> ORGANISM: Artificial
<220> FEATURE:
<223> OTHER INFORMATION: Primer

<400> SEQUENCE: 22
acaggtgttg gtgtttgctc ac                                          22

```
<210> SEQ ID NO 23
<211> LENGTH: 22
<212> TYPE: DNA
<213> ORGANISM: Artificial
<220> FEATURE:
<223> OTHER INFORMATION: Primer

<400> SEQUENCE: 23
tcagatgcgt ttacgagaca gg                                              22

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
taactgctcg cggatgagtg                                                 20

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
agaatgaggc tgaagccctc                                                 20

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
gtgatctcat gctgcaggct                                                 20

<210> SEQ ID NO 27
<211> LENGTH: 179
<212> TYPE: DNA
<213> ORGANISM: Equus caballus

<400> SEQUENCE: 27
gtcgcagaag aggagccatg agaatgaggc tgaagccctc cgcggggaga tccagagcct     60
gaaggaggag aacaaccggc agcagcagct gctggcccag aacctgcagc tgccccccaga   120 ggcccgcatc gaggccagcc tgcagcatga gatcacccgg ctgaccaacg aaaacttgg    179

<210> SEQ ID NO 28
<211> LENGTH: 178
<212> TYPE: DNA
<213> ORGANISM: Equus caballus

<400> SEQUENCE: 28
gtcgcagaag aggagccatg agaatgaggc tgaagccctc cgcggggaga tccagagcct     60
gaaggaggag aacaaccggc agcagcagct gctggcccag aacctgcagc tgccccccaga   120 ggccgcatcg aggccagcct gcagcatgag atcacccggc tgaccaacga aaacttgg     178
```

OLIGONUCLEOTIDES AND METHODS FOR DETECTING LAVENDER FOAL SYNDROME

PRIORITY CLAIM

This patent application is a U.S. National Phase of International Patent Application No. PCT/IB2010/055529, filed 1 Dec. 2010, which claims priority to South African Patent Application No. 2009/08541, filed 2 Dec. 2009, the disclosures of which are incorporated herein by reference in their entirety.

FIELD

The presently disclosed embodiments relate to the detection of genetic abnormalities associated with animal pathologies. More specifically, the disclosed embodiments provide a method for detecting a polymorphism associated with Lavender Foal Syndrome (or a predisposition thereto), to a diagnostic test for Lavender Foal Syndrome, to oligonucleotides for detecting Lavender Foal Syndrome, and to a diagnostic kit.

BACKGROUND

Lavender Foal Syndrome is an autosomal recessive lethal disorder affecting Arabian foals which is also characterised by a dilute coat colour and severe neurological signs.

Lavender Foal syndrome (LFS), also referred to as dilute lethal (Bowling 1996), lethal LFS (Schott II & Petersen 2005), and coat colour dilution lethal (Fanelli 2005) is a condition only reported to affect Arabian foals (Bowling 1996; Fanelli 2005; Madigan 1997; Pascoe & Knottenbelt 1999) inherited in an autosomal recessive manner (Bowling 1996). Affected foals have an unusual dilute coat colour, demonstrate various neurological abnormalities, are not able to stand and nurse, and if the typical coat colour characteristic is overlooked may be incorrectly diagnosed as suffering from neonatal maladjustment syndrome (NMS), neonatal septicaemia or neonatal encephalopathy (Bowling 1996; Page et al. 2006). Post mortem evaluations have failed to yield any macroscopic findings, suggesting a biochemical cause for LFS. The prevalence of LFS remains unknown (Fanelli 2005; Page et al. 2006). A recent study using SNP chip technology has allowed researchers to identify a candidate region of 1 Mb containing 216 candidate genes for the disease (Gabreski et al. 2009). The disclosed embodiments locate genetic markers associated with the disease.

SUMMARY

Broadly, according to at least one disclosed embodiment, there is provided a method for detecting a genetic polymorphism associated with Lavender Foal Syndrome or a predisposition thereto, the method comprising the step of screening a subject for the presence of at least one polymorphism in the MYO5A gene family, or derivatives thereof.

The method may include the steps of obtaining a specimen from the subject, the specimen containing genomic material; and sequencing the specimen to detect the presence of a mutation or polymorphism which may result in the truncation or incorrect expression of the MYO5A gene.

More particularly, sequencing may be performed to detect the presence of a frameshift deletion which may result in a premature stop codon. More particularly, the mutation may be a c.4459delC mutation.

Alternatively, or additionally, the method may include the step of detecting an interaction between a target sequence present in the genomic material and an isolated molecular marker selected from the group comprising any one or more of SEQ. ID. NOs. 13, 14, and 28, sequences complementary thereto, sequences which can hybridize under strict hybridization conditions thereto, functional truncations thereof, and sequences having at least 75% or greater homology thereto.

In at least one disclosed embodiment, there is provided a method for detecting a genetic polymorphism associated with Lavender Foal Syndrome or a predisposition thereto in a subject, the method comprising the step of screening a genomic material sample from the subject for the presence of at least one polymorphism in the MYO5A gene family, or derivatives thereof.

In another disclosed embodiment there is provided a method for detecting Lavender Foal Syndrome or a predisposition thereto or genetic carrier status thereof in a subject, the method comprising the step of detecting in a nucleic acid sample from the subject the presence or absence of at least one genetic polymorphism in a MYO5A gene, wherein the presence of the at least one polymorphism in the MYO5A gene is indicative of Lavender Foal Syndrome or a predisposition thereto or genetic carrier status thereof in the subject.

In a further disclosed embodiment there is provided a method for detecting for detecting Lavender Foal Syndrome or a predisposition thereto or genetic carrier status thereof in a subject, the method comprising the step of detecting in a nucleic acid sample from the subject the allelic status of at least one genetic polymorphism in a MYO5A gene, wherein an allelic status of homozygosity is indicative of Lavender Foal Syndrome or a predisposition thereto in the subject, and wherein an allelic status of heterozygocity is indicative of a carrier status thereof in the subject.

The isolated molecular marker may have at least 85%, 95%, 99%, or 100% homology to the MYO5A gene containing the c.4459delC mutation.

The method may include hybridising any one or more of the markers of SEQ. ID. NOs. 13, 14, and 28 to the genomic complement and screening for a desired interaction, or the presence of a mutation. The method further may include the step of subjecting the specimen to polynucleotide amplification using a primer pair comprising at least SEQ. ID. NO. 13, or SEQ. NO. 14. Optionally, the primer pair comprises SEQ. ID. NO. 13 and SEQ. ID. NO. 14, and screening is then done to detect the presence of a 153 bp product.

According to yet another disclosed embodiment, there is provided an isolated molecular marker for use in detecting the presence of a mutation associated with a predisposition to, or increased risk for, Lavender Foal Syndrome, the molecular marker comprising at least one isolated nucleic acid fragment derived from a MYO5A gene and containing the c.4459delC mutation, flanking sequences thereof, sequences complementary thereto, sequences which can hybridize under strict hybridization conditions thereto, functional discriminatory truncations thereof, or sequences having at least 75% or greater homology thereto.

The isolated molecular marker may have at least 85%, 95%, 99%, or 100% homology to the MYO5A gene containing the c.4459delC mutation.

The isolated molecular marker may be DNA-based, RNA-based, or other suitable combinations of nucleic acids or modified bases, suitably isolated or purified.

The isolated molecular marker may be a part of, or a fragment derived from, an MYO5A gene and containing the c.4459delC mutation, the fragment being between 10 and 40, optionally between 15 and 35, or between 20 and 30 nucleic acids in length, and which hybridizes under stringent hybridization conditions to at least a portion of the MYO5A gene. This may include sequences complementary to the marker, and sequences having substitutions, deletions or insertions, sequences which can hybridize under strict hybridization conditions thereto, functional discriminatory truncations thereof, and sequences having at least 75% or greater homology thereto. As such, the fragment may be a fragment of SEQ. ID. NO. 28 comprising at least the c.4459delC mutation, or flanking sequences.

In at least one disclosed embodiment, the isolated molecular marker may be a polymorphic marker, an SNP, short tandem repeat, microsatellite marker, or other suitable markers. The SNP may be an SNP comprising a c.4459delC mutation, together with any other SNP closely linked (i.e. which is in high linkage disequilibrium) with the c.4459delC mutation SNP.

Accordingly, the disclosed embodiments extend to a primer or oligonucleotide set for use in detecting or diagnosing a predisposition to, or increased risk for, Lavender Foal Syndrome, the primer or oligonucleotide set comprising isolated nucleic acid sequences selected from at least SEQ. ID. NO. 13 or SEQ. ID. NO. 14, optionally both SEQ. ID. NOs. 13 and 14; sequences complementary thereto, sequences which can hybridize under stringent hybridization conditions thereto, and functional discriminatory truncations thereof.

In a disclosed embodiment, the isolated molecular marker is an isolated nucleic acid molecule selected from the group comprising a nucleic acid fragment having a sequence derived from a MYO5A gene and containing the c.4459delC polymorphism, SEQ ID NO 13, SEQ ID NO 14, SEQ ID NO 28, and sequences complementary thereto.

The disclosed embodiments encompass an amplified polynucleotide having a Single Nucleotide Polymorphism (SNP) at a position corresponding to the c.4459delC polymorphism in a MYO5A gene.

The amplified polynucleotide may have a length ranging from about 3 nucleotides at the position corresponding to c.4459delC where the position corresponding to c.4459delC is flanked on the 5' and 3' side by one or more nucleotides. The amplified polynucleotide may have a length of between about 3 to 300 nucleotides. Optionally, the amplified polynucleotide has a length of between 153 to 154 nucleotides.

The disclosed embodiments extend also to a detection reagent capable of detecting one or more single nucleic acid polymorphisms selected from the group consisting of the SNP(s) listed hereinbefore, fragments thereof, sequences complementary thereto, sequences which can hybridize under stringent hybridization conditions thereto, and functional discriminatory truncations thereof.

The disclosed embodiments extend to the use of the sequences and/or, molecular markers or amplified polynucleotides in other assays, such as RFLPs and AFLPs, Short Tandem Repeats, or SNPs.

According to another disclosed embodiment, there is provided a diagnostic assay comprising any one or more of the markers described hereinbefore, fragments thereof, sequences complementary thereto, sequences which can hybridize under stringent hybridization conditions thereto, and functional discriminatory truncations thereof.

According to a still further disclosed embodiment, there is provided a kit for use in detecting a mutation associated with Lavender Foal Syndrome in a subject, the kit comprising any one or more of the isolated molecular markers or oligonucleotides selected to detect a c.4459delC mutation; and suitable reaction media.

The kit may further include any one or more of reagents, such as buffers, DNases, RNAses, polymerases, instructions, and the like.

The isolated molecular markers may be any one or more markers selected from the markers listed hereinbefore.

Further disclosed embodiments will now be described, with reference to the following non-limiting examples and drawing.

BRIEF DESCRIPTION OF THE DRAWING

In the drawing:
FIG. 1 shows a single-base deletion of MYO5A, causing the p.Arg1487AlafsX12 mutation. a) Schematic representation of myosin Va (myoVa) protein sequence. The deletion results in a frame shift with a premature stop codon 12 residues from the deletion. b) Electropherograms of sequencing data (left) show the deletion of C in affected and carrier individuals and fragment analysis (right) highlights the heterozygous nature of the carrier animals as can be seen from the two peaks.

The DNA sequences of SEQ ID NOs 1-128 are set out in Table 1 below.

DETAILED DESCRIPTION

For the purposes of this specification, a "polymorphism" may include a change or difference between two related nucleic acids. A "nucleotide polymorphism" refers to a nucleotide which is different in one sequence when compared to a related sequence when the two nucleic acids are aligned for maximal correspondence. A "probe" or "molecular marker" is an RNA sequence(s) or DNA sequence(s) or analogues, modified versions, or the complement of the sequences shown. This may include a "genetic marker", which is a region on a genomic nucleic acid mapped by a molecular marker or probe. A "probe" is a composition labelled with a detectable label. A "probe" is typically used herein to identify a marker nucleic acid. A polynucleotide probe is usually a single-stranded nucleic acid sequence that can be used to identify complementary nucleic acid sequences, or may be a double- or higher order-stranded nucleic acid sequence which can be used to bind to, or associate with, a target sequence or area, generally following denaturing. The sequence of the polynucleotide probe may or may not be known. An RNA probe may hybridize with its corresponding DNA gene, or to a complementary RNA, or to other type of nucleic acid molecules. As used herein the term "functional discriminatory truncations" mean nucleic acid sequences, modified nucleic acid sequences, or other nucleic acid variants which, although they are truncated forms of sequences presented herein or variants thereof, can still bind in a discriminatory manner to target gene or nucleic acid sequences described herein and forming part of the disclosed embodiments. The terms "isolated" or "biologically pure" refer to material which is substantially or essentially free from components which normally accompany it as found in its native state. An "amplified mixture" of nucleic acids includes multiple copies of more than one (and generally several) nucleic acids. "Stringent hybridization conditions" in the context of nucleic acid hybridization are sequence dependent and are different under different environmental parameters. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Highly stringent conditions are selected to be equal to the $T_m$ point for a particular probe. An example of stringent wash conditions for, say, a Southern blot of such nucleic acids is a 0.2×SSC wash at 65° C. for 15 minutes. Such a high stringency wash may be preceded by a low stringency wash to remove background probe signal. An example of a low stringency wash is 2×SSC at 40° C. for 15 minutes. In general, a signal to noise ratio of 2× (or higher) than that observed for an unrelated probe in the particular hybridization assay indicates detection of a specific hybridization event. For highly specific hybridization strategies such as allele-specific hybridization, an allele-specific probe is usually hybridized to a marker nucleic acid (e.g., a genomic nucleic acid, an amplicon, or the like) comprising a polymorphic nucleotide under highly stringent conditions.

Preliminary investigations had indicated that MYO5A may be a possible candidate gene for Lavender Foal Syndrome. Sequencing of the coding region identified a single-base deletion in a conserved region of the tail domain. The deletion produces a truncated protein product through the insertion of a premature stop codon (p.Arg1487AlafsX12). The deletion was confirmed as the causative mutation by genotyping affected, carrier and normal individuals.

Materials and Methods

To identify the molecular defect underlying this disorder, the coding region of the MYO5A gene in normal, affected and carrier animals was sequenced. DNA was extracted from tissue and blood samples of four affected foals, their carrier sires and dams as well as four unaffected, non-carrier individuals using a phenol-chloroform DNA extraction protocol with ethanol washes. PCR amplification of the MYO5A coding region was done using 12 sets of primers (SEQ. ID. NOs. 1 to 24, also referred to as Lavender 1 to Lavender 12 in Table 1), designed to amplify 12 regions of coding sequence conserved between *Mus musculus* and *Equus caballus*. PCR amplification was performed for 35 cycles of 45 s at 95° C., 1 min at 60° C. and 2 min at 72° C. with a final extension step of 8 min at 72° C. in 20 μl reaction volumes. PCR products were purified using the Invitek MSB Spin PCRapace Kit by Invisorb® and sequenced in 10 μl reactions using Bigdye v3.1 sequencing chemistry (Applied Biosystems) on the ABI 3130×1 Genetic Analyzer (Applied Biosystems). Partial sequences of the MYO5A gene of normal and affected individuals are attached as Sequence 1 (also referred to as SEQ. ID. NO. 27) and Sequence 2 (also referred to as SEQ. ID. NO. 28), respectively.

TABLE 1

List of primers used for sequencing and genotyping

| | | | | | |
|---|---|---|---|---|---|
| Lavender1 | SEQ.ID.NO. 1 | F:5'-aagacaaagcgcatgccacc-3' | SEQ.ID.NO. 2 | R:5'-gccgcattcttcagcatcca-3' | |
| Lavender2 | SEQ.ID.NO. 3 | F:5'-tccagatgctgtgtcttgtgca-3' | SEQ.ID.NO. 4 | R:5'-tcacagtccactcagacagcaa-3' | |
| Lavender3 | SEQ.ID.NO. 5 | F:5'-tacagtggtcagaacatgggtg-3' | SEQ.ID.NO. 6 | R:5'-aaacagagcttccaccaacc-3' | |
| Lavender4 | SEQ.ID.NO. 7 | F:5'-gctggaatccttcacttaggca-3' | SEQ.ID.NO. 8 | R:5'-acaggtattgtgcagctgtc-3' | |
| Lavender5 | SEQ.ID.NO. 9 | F:5'-tgactatgggcaaagtgcagg-3' | SEQ.ID.NO. 10 | R:5'-gtaggaacctctcccatcagga-3' | |
| Lavender6 | SEQ.ID.NO. 11 | F:5'-ccttgcagatactccgtgagca-3' | SEQ.ID.NO. 12 | R:5'-atgctccacttctagggctc-3' | |
| Lavender7 | SEQ.ID.NO. 13 | F:5'-ctagggtcatctccgtttccta-3' | SEQ.ID.NO. 14 | R:5'-ccaagttttcgttggtcagc-3' | |
| Lavender8 | SEQ.ID.NO. 15 | F:5'-tttagccagatggtggctccac-3' | SEQ.ID.NO. 16 | R:5'-tttccactccacagagaccagg-3' | |
| Lavender9 | SEQ.ID.NO. 17 | F:5'-accaggattcacatgtccccac-3' | SEQ.ID.NO. 18 | R:5'-aaggtgtcggttaagactggga-3' | |
| Lavender10 | SEQ.ID.NO. 19 | F:5' gttgcattgacattgctgttgg-3' | SEQ.ID.NO. 20 | R:5'-atctactggtgggcacatgagg-3' | |
| Lavender11 | SEQ.ID.NO. 21 | F:5'-agcacacgaacttaaccactcg-3' | SEQ.ID.NO. 22 | R:5'-acaggtgttggtgtttgctcac-3' | |
| Lavender12 | SEQ.ID.NO. 23 | F:5'-tcagatgcgtttacgagacagg-3' | SEQ.ID.NO. 24 | R:5'-taactgctcgcggatgagtg-3' | |

TABLE 1-continued

List of primers used for sequencing and genotyping

| ACDF01 | SEQ.ID.NO. 25 | F:5'-agaatgaggctgaagcctc-3' | SEQ.ID.NO. 26 | BR:5'-gtgatctcatgctgcaggct-3' |
|---|---|---|---|---|

SEQ. ID. NO. 27:

Partial Sequence of MYO5A Gene from a Normal Horse.

```
GTCGCAGAAG AGGAGCCATG AGAATGAGGC TGAAGCCCTC
CGCGGGGAGA TCCAGAGCCT GAAGGAGGAG AACAACCGGC
AGCAGCAGCT GCTGGCCCAG AACCTGCAGC TGCCCCCAGA
GGCCCGCATC GAGGCCAGCC TGCAGCATGA GATCACCCGG
CTGACCAACG AAAACTTGG
```

SEQ. ID. NO. 28:

Partial Sequence of MYO5A Gene from an Affected Horse with the c.4459delC Mutation which Causes Lavender Foal Syndrome. "-" indicates the single-base deletion of cytosine at 4459 bp (c.4459delC) which produced a frameshift that resulted in a premature stop codon (p.Arg1487AlafsX12).

```
GTCGCAGAAG AGGAGCCATG AGAATGAGGC TGAAGCCCTC
CGCGGGGAGA TCCAGAGCCT GAAGGAGGAG AACAACCGGC
AGCAGCAGCT GCTGGCCCAG AACCTGCAGC TGCCCCCAGA
GGCC-GCATC GAGGCCAGCC TGCAGCATGA GATCACCCGG
CTGACCAACG AAAACTTGG
```

Results

Comparison of the nucleotide sequences between affected and normal individuals revealed only one sequence variation in the fragment amplified by primer set 7 ("Lavender7"), i.e. SEQ. ID. NO. 13 and 14. A single-base deletion of cytosine at 4459 bp (c.4459delC) produced a frameshift that resulted in a premature stop codon (p.Arg1487AlafsX12). The substituted amino acid, Arginine, is conserved between human, mouse, rat and horse sequences and the resulting truncation of almost half the protein tail (FIG. 1) is the causative mutation for the disorder. Direct sequencing of the region containing the deletion confirmed that affected and carrier individuals were homozygous and heterozygous for the deletion, respectively, while the deletion did not occur in normal individuals (FIG. 1). In order to confirm the specificity of the mutation, 29 samples from individuals related to the four carrier foals as well as 5 unrelated control samples were genotyped. Fluorescently labelled primers were designed to amplify a 154 bp fragment flanking the deletion site (ACDF01 in Table 1 of supplementary data). PCR amplification was performed for 35 cycles of 45 s at 95° C., 45 s at 60° C. and 1 min at 72° C. with a final extension step of 8 min at 72° C. in 20 µl reaction volumes. PCR products were subjected to capillary electrophoresis using an ABI 3130x1 Genetic Analyzer (Applied Biosystems). Affected individuals all showed a single peak with a fragment length of 153 bp on STRand software (University of California; 2006; version 2.4.16) while normal individuals had a single peak at 154 bp. Heterozygous carriers had two characteristic peaks of 153 bp and 154 bp (FIG. 1).

Discussion

Myosins are cargo binding proteins that move along actin filaments, amongst others, driven by ATP hydrolysis (Woolner & Bement 2009). Myosin Va (MyoVa) is expressed in the brain and skin (Takagishi & Murata 2006) where it functions in organelle transport and membrane trafficking (Reck-Peterson et al. 2000). Diluted mouse and rat mutants have defects in melanosome transport and a failure of their release into keratinocytes (Futaki et al. 2000; Takagishi & Murata 2006). MyoVa also plays a role in axonal and dendritic transport in neurons (Langford & Molyneaux 1998; Reck-Peterson et al. 2000). In man, Griscelli syndrome type I is an autosomal recessive genetic disorder associated with a mutation in MYO5A which is characterised by pigmentary dilution with hypotonia, marked motor developmental delay and mental retardation (Pastural et al. 1997).

The myosin heavy chain consists of an N-terminal globular head that is conserved across the class V myosins, a neck region with an alpha-helical structure and a tail domain consisting of a helical coiled-coil interspersed with globular domains and ending in a C-terminal globular tail. The head of the protein contains sites for ATP hydrolysis and actin binding and is approximately 765 amino acids in length. The neck region of approximately 147 amino acids contains the calmodulin binding sites in the form of six IQ motifs (Sellers 2000). The alpha-helical tail is the site of dimerization while its distal globular segment is responsible for cargo binding and protein localization (Langford & Molyneaux 1998). The globular tail of MyoVa contains at least two separate binding sites with a high propensity for interacting with a wide range of different cargo molecules (Li & Nebenführ 2008). Alternative splicing in the coiled-coil of the tail region creates further cargo binding specificity in that different exons, with different binding domains, are expressed in specific tissues only. The brain isoform contains exon B with a binding domain for adaptors in the brain while in the skin exons D and F code for binding domains for melanophillin (Au & Huang 2002).

The c.4459delC mutation described here lies within the globular tail domain of the MyoVa protein. The region where the c.4459delC mutation lies is within a deletion of a mouse mutant, D20J, which is known to occur in all splice variants (Strobel et al. 1990). Mice homozygous for the dilute mutation have dilute coat colour, show severe ataxia and opisthotonus and die within three weeks (Huang et al. 1998). The neurological aspect of the condition arises from aberrant transport of organelles in the neurons which in turn impairs synaptic regulation (Takagishi et al. 2007). The dilute colour observed is not due to abnormal pigment production but an abnormal dispersal of melanosomes within the hair shafts (Au & Huang 2002; Strobel et al. 1990).

Griscelli syndrome type 1 in man is associated with pigment dilution and neurological symptoms (Pastural et al. 1997) while the dilute lethal mouse and dilute-opisthotonus rat mutants exhibit dilute coat colours and intermittent opisthotonus (Futaki et al. 2000; Huang et al. 1998). The present disclosure provides evidence that Lavender Foal Syndrome is an autosomal recessive condition caused by a single-base deletion in the MYO5A gene on chromosome 1 of equines.

Surprisingly, the inventors uncovered not the well known dilute mouse deletion, D20J, which one would expect to find in the coding sequence examined because it is conserved between *Mus musculus* and *Equus caballus*, but the novel c.4459delC polymorphism set out hereinbefore. The disclosed embodiments therefore provide a novel genetic marker associated with Lavender Foal Syndrome.

References

Au, J. S. Y. & Huang, J. D. 2002. A tissue-specific exon of Myosin Va is responsible for selective cargo binding in melanocytes. *Cell Motility and the Cytoskeleton*, 53, (2) 89-102

Bowling, A. T. 1996, "Medical genetics," *In Horse Genetics*, Wallingford: CAB International, pp. 105-106.

Fanelli, H. H. 2005. Coat colour dilution lethal ('lavender foal syndrome'): A tetany syndrome of Arabian foals. *Equine Veterinary Education*, 17, (5) 260-263

Futaki, S., Takagishi, Y., Hayashi, Y., Ohmori, S., Kanou, Y., Inouye, M., Oda, S. I., Seo, H., Iwaikawa, Y., & Murata, Y. 2000. Identification of a novel myosin-Va mutation in an ataxic mutant rat, dilute-opisthotonus. *Mammalian Genome*, 11, (8) 649-655

Gabreski, N., Brooks, S., Miller, D., & Anczak, D. 2009. Mapping of Lavender Foal Syndrome using the EquineSNP50 Chip. *Journal of Equine Veterinary Science*, 29, (5) 321-322

Huang, J. D., Mermall, V., Strobel, M. C., Russell, L. B., Mooseker, M. S., Copeland, N. G., & Jenkins, N. A. 1998. Molecular genetic dissection of mouse unconventional myosin-VA: Tail region mutations. *Genetics*, 148, (4) 1963-1972

Langford, G. M. & Molyneaux, B. J. 1998. Myosin V in the brain: mutations lead to neurological defects. *Brain Research Reviews*, 28, 1-8

Li, J. F. & Nebenführ, A. 2008. The tail that wags the Dog: The globular Tail Domain defines the function of Myosin V/XI. *Traffic*, 9, (3) 290-298

Madigan, J. E. 1997, "Congenital anomalies and genetic disorders," *In Manual of Equine Neonatal Medicine*, Woodland, Calif.: Live Oak Publishing, pp. 210-211.

Page, P., Parker, R., Harper, C., Guthrie, A., & Neser, J. 2006. Clinical, clinicopathologic, postmortem examination findings and familial history of 3 Arabians with lavender foal syndrome. *Journal of Veterinary Internal Medicine*, 20, (6) 1491-1494

Pascoe, R. R. & Knottenbelt, D. C. 1999, "Congenital/developmental diseases," *In Manual of Equine Dermatology*, London: WB Saunders Co, pp. 148-149.

Pastural, E., Barrat, F. J., Dufourcq-Lagelouse, R., Certain, S., Sanal, O., Jabado, N., Seger, R., Griscelli, C., Fischer, A., & De Saint Basile, G. 1997. Griscelli disease maps to chromosome 15q21 and is associated with mutations in the myosin-Va gene. *Nature Genetics*, 16, (3) 289-292

Reck-Peterson, S. L., Provance, D. W., Mooseker, M. S., & Mercer, J. A. 2000. Class V myosins. *Biochimica et Biophysica Acta (BBA)—Molecular Cell Research*, 1496, (1) 36-51

Schott II, H. C. & Petersen, A. D. 2005. Cutaneous markers of disorders affecting young horses. *Clinical Techniques in Equine Practice*, 4, (4) 314-323

Sellers, J. R. 2000. Myosins: a diverse superfamily. *Biochimica et Biophysica Acta*, 1496, (1) 3

Strobel, M. C., Seperack, P. K., Copeland, N. G., & Jenkins, N. A. 1990. Molecular analysis of two mouse dilute locus deletion mutations: spontaneous dilute lethal20J and radiation-induced dilute prenatal lethal Aa2 alleles. *Molecular and Cellular Biology*, 10, (2) 501-509

Takagishi, Y., Hashimoto, K., Kayahara, T., Watanabe, M., Otsuka, H., Mizoguchi, A., Kano, M., & Murata, Y. 2007. Diminished climbing fiber innervation of Purkinje cells in the cerebellum of myosin Va mutant mice and rats. *Developmental Neurobiology*, 67, (7) 909-923

Takagishi, Y. & Murata, Y. 2006. Myosin Va mutation in rats is an animal model for the human hereditary neurological disease, Griscelli Syndrome Type 1. *Annals of the New York Academy of Science*, 1086, 66-80

Woolner, S. & Bement, W. M. 2009. Unconventional myosins acting unconventionally. *Trends in Cell Biology*, 19, (6) 245-252

The invention claimed is:

1. A method for detecting a genetic polymorphism associated with Lavender Foal Syndrome or a carrier thereto in an Arabian horse, the method comprising:
   amplifying a genomic material sample from the Arabian horse with labeled primers to detect the presence of a polymorphism in a MYO5A gene, wherein the polymorphism is c.4459delC and is a frameshift deletion causing a premature stop codon; and
   subjecting the amplified genomic material to capillary electrophoresis wherein one peak detects an affected horse and 2 peaks detect a carrier horse.

2. A method for detecting Lavender Foal Syndrome or a predisposition thereto or genetic carrier status thereof in an Arabian horse, the method comprising:
   obtaining a sample containing nucleic acid of an Arabian horse;
   isolating a nucleic acid sample from the sample containing nucleic acid of an Arabian horse;
   detecting in the nucleic acid sample from the Arabian horse the presence or absence of a c.4459delC polymorphism in a MYO5A gene, by hybridizing to the nucleic acid sample from the Arabian horse an isolated nucleic acid molecule having a sequence selected from the group consisting of any one or more of SEQ. ID. NOs. 13, 14, and 28, sequences complementary thereto, and
   diagnosing the Arabian horse with Lavender Foal Syndrome or a predisposition thereto or genetic carrier status thereof, wherein the presence of the c.4459delC polymorphism in the MYO5A gene is indicative of Lavender Foal Syndrome or a predisposition thereto or genetic carrier status thereof in the Arabian horse.

3. The method as claimed in claim 2, in which detecting in the nucleic acid sample from the Arabian horse the presence or absence of at least one genetic polymorphism, comprises providing a reaction mixture comprising
   a) the nucleic acid sample, in which the nucleic acid sample is in the form of a double-stranded target DNA
   b) a pair of primers comprising SEQ. ID. NOs. 13 and 14 wherein the first primer is complementary to a sequence on the first strand of the target DNA and the second primer is complementary to a sequence on the second strand of DNA,
   c) a heat-stable DNA polymerase, and
   d) a plurality of free nucleotides;
   using the reaction mixture to perform PCR (Polymerase Chain Reaction) amplification and produce a product or products of the said PCR amplification; and
   visualizing the product or products of the said PCR amplification.

4. A method as claimed in claim 3, in which the pair of primers are labeled, and where visualizing the product or products of the said PCR amplification comprises subjecting the product or products to gel electrophoresis.

5. A method as claimed in claim 2, in which detecting in the nucleic acid sample from the Arabian horse the presence or absence of at least one genetic polymorphism, comprises:
   providing a reaction mixture comprising
   a) the nucleic acid sample, in which the nucleic acid sample is in the form of a double-stranded target DNA,
   b) an isolated nucleic acid molecule having a sequence selected from the group comprising any one or more of SEQ. ID. NOs. 13, 14, and 28, sequences complementary thereto,
   c) a heat-stable DNA polymerase, and
   d) a plurality of free nucleotides;
   using the reaction mixture to perform PCR (Polymerase Chain Reaction) amplification and produce a product or products of the said PCR amplification; and
   sequencing the product or products of the said PCR amplification to visualize differences between a normal sequence and a sequence which includes the c.4459delC polymorphism.

6. The method as claimed in claim 2, in which the method for detecting Lavender Foal Syndrome or a predisposition thereto or genetic carrier status thereof in an Arabian horse comprises,
   detecting the allelic status of the genetic polymorphism in a MYO5A gene,
   wherein an allelic status of homozygosity is indicative of Lavender Foal Syndrome or a predisposition thereto in the Arabian horse, and
   wherein an allelic status of heterozygosity is indicative of a carrier status thereof in the Arabian horse, and wherein such information is useful for horse breeding.

* * * * *